(12) United States Patent
Mirakyan

(10) Patent No.: US 8,579,030 B2
(45) Date of Patent: Nov. 12, 2013

(54) TRIGGERED POLYMER VISCOUS PILL AND METHODS OF USING THE SAME

(75) Inventor: Andrey Mirakyan, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 282 days.

(21) Appl. No.: 12/976,395

(22) Filed: Dec. 22, 2010

(65) Prior Publication Data

US 2012/0160519 A1 Jun. 28, 2012

(51) Int. Cl.
*E21B 43/22* (2006.01)
*E21B 43/27* (2006.01)

(52) U.S. Cl.
USPC .............................. 166/281; 166/282; 166/307

(58) Field of Classification Search
None
See application file for complete search history.

(56) References Cited

U.S. PATENT DOCUMENTS

| | | | |
|---|---|---|---|
| 5,203,834 A | 4/1993 | Hutchins et al. | |
| 5,486,312 A | 1/1996 | Sandiford et al. | |
| 2006/0054324 A1 | 3/2006 | Sullivan et al. | |
| 2008/0280788 A1 | 11/2008 | Parris et al. | |
| 2008/0280790 A1 | 11/2008 | Mirakyan et al. | |
| 2009/0247430 A1* | 10/2009 | Fu | 507/211 |
| 2010/0081586 A1 | 4/2010 | Smith et al. | |
| 2010/0184630 A1 | 7/2010 | Sullivan et al. | |
| 2010/0276150 A1 | 11/2010 | Sullivan et al. | |
| 2011/0082057 A1* | 4/2011 | Zhang et al. | 507/90 |

OTHER PUBLICATIONS

International Search Report and Written Opinion issued in PCT/IB2011/055833 on Aug. 7, 2012, 12 pages.

* cited by examiner

*Primary Examiner* — Zakiya W Bates
(74) *Attorney, Agent, or Firm* — Jeremy Tillman; Daryl R. Wright; Tim Curington

(57) ABSTRACT

The invention provides a method comprising providing a composition comprising a pH trigger and a polymer able to be hydrated in a defined pH zone; injecting the composition with a pH outside the defined pH zone; triggering the pH trigger to adjust the pH of the composition within the defined pH zone; and allowing viscosity of the composition to increase and form a plug.

23 Claims, 3 Drawing Sheets

TRIGGERED POLYMER VISCOUS PILL AND METHODS OF USING THE SAME

FIELD OF THE INVENTION

The invention relates generally to the exploitation of hydrocarbon-containing formations or injection wells. More specifically, the invention relates to chemical zonal isolation or diversion and relies on hydration properties of certain biopolymers, mostly guar derivatives.

BACKGROUND

The statements in this section merely provide background information related to the present disclosure and may not constitute prior art.

Hydrocarbons (oil, condensate, and gas) are typically produced from wells that are drilled into the formations containing them. For a variety of reasons, such as inherently low permeability of the reservoirs or damage to the formation caused by drilling and completion of the well, the flow of hydrocarbons into the well is undesirably low. In this case, the well is "stimulated," for example using hydraulic fracturing, chemical (usually acid) stimulation, or a combination of the two (called acid fracturing or fracture acidizing).

Hydraulic fracturing involves injecting fluids into a formation at high pressures and rates such that the reservoir rock fails and forms a fracture (or fracture network). Proppants are typically injected in fracturing fluids after the pad to hold the fracture(s) open after the pressures are released. In chemical (acid) stimulation treatments, flow capacity is improved by dissolving materials in the formation.

In hydraulic and acid fracturing, a first, viscous fluid called a "pad" is typically injected into the formation to initiate and propagate the fracture. This is followed by a second fluid that contains a proppant to keep the fracture open after the pumping pressure is released. Granular proppant materials may include sand, ceramic beads, or other materials. In "acid" fracturing, the second fluid contains an acid or other chemical such as a chelating agent that can dissolve part of the rock, causing irregular etching of the fracture face and removal of some of the mineral matter, resulting in the fracture not completely closing when the pumping is stopped. Occasionally, hydraulic fracturing is done without a highly viscosified fluid (i.e., slick water) to minimize the damage caused by polymers or the cost of other viscosifiers.

When multiple hydrocarbon-bearing zones are stimulated by hydraulic fracturing or chemical stimulation, it is desirable to treat the multiple zones in multiple stages. In multiple zone fracturing, a first pay zone is fractured. Then, the fracturing fluid is diverted to the next stage to fracture the next pay zone. The process is repeated until all pay zones are fractured. Alternatively, several pay zones may be fractured at one time, if they are closely located with similar properties. Diversion may be achieved with various techniques including formation of a temporary plug using polymer gels or solid fluid loss materials.

Polymer gels have been widely used for conformance control of naturally fissured/fractured reservoirs. For an overview of existing polymer compositions, reference is made to the U.S. Pat. Nos. 5,486,312 and 5,203,834 which also list a number of patents and other sources related to gel-forming polymers.

The applicants found a method of triggering and controlling the formation of plugs.

SUMMARY

In a first aspect, a method is disclosed. The method comprises providing a composition comprising a pH trigger and a polymer able to be hydrated in a defined pH zone; injecting the composition with a pH outside the defined pH zone; triggering the pH trigger to adjust the pH of the composition within the defined pH zone; and allowing viscosity of the composition to increase and form a plug.

In a second aspect, a method of treating a subterranean formation in a wellbore is disclosed. The method comprises providing a composition comprising a polymer able to be hydrated in a defined pH zone; injecting the composition with a pH outside the defined pH zone; providing a pH trigger; triggering the pH trigger to adjust the pH of the composition within the defined pH zone; and allowing viscosity of the composition to increase and form a plug.

In a third aspect, a method of zonal isolation or diversion in a wellbore is disclosed. The method comprises providing a composition comprising a polymer able to be hydrated in a defined pH zone; injecting the composition with a pH outside the defined pH zone in the wellbore; providing a pH trigger; triggering the pH trigger to adjust the pH of the composition within the defined pH zone; and allowing viscosity of the composition to increase and form a plug.

DETAILED DESCRIPTION

Figure 1:
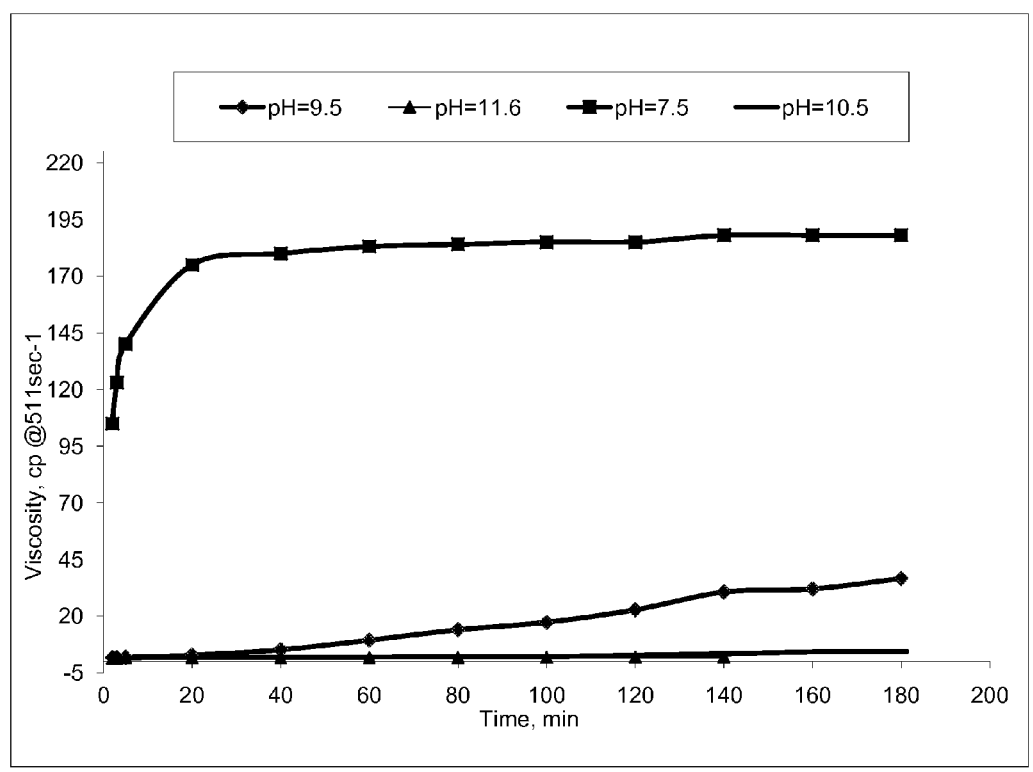
FIG. 1 is a graph showing hydration rates of CMHPG at different pH.

At the outset, it should be noted that in the development of any actual embodiments, numerous implementation-specific decisions must be made to achieve the developer's specific goals, such as compliance with system and business related constraints, which can vary from one implementation to another. Moreover, it will be appreciated that such a development effort might be complex and time consuming but would nevertheless be a routine undertaking for those of ordinary skill in the art having the benefit of this disclosure.

The description and examples are presented solely for the purpose of illustrating embodiments of the invention and should not be construed as a limitation to the scope and applicability of the invention. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possession of the entire range and all points within the range disclosed and enabled the entire range and all points within the range.

The following definitions are provided in order to aid those skilled in the art in understanding the detailed description of the invention.

The term "fracturing" refers to the process and methods of breaking down a geological formation and creating a fracture, i.e. the rock formation around a well bore, by pumping fluid at very high pressures, in order to increase production rates from a hydrocarbon reservoir. The fracturing methods otherwise use conventional techniques known in the art.

According to a first embodiment, the method comprises providing a composition comprising a pH trigger and a polymer able to be hydrated in a defined pH zone; injecting the composition with a pH outside the defined pH zone; triggering the pH trigger to adjust the pH of the composition within the defined pH zone; and allowing viscosity of the composition to increase and form a plug.

The defined pH zone is between about pH 0 and about pH 8.5, or between about pH 2 and about pH 8, or between about pH 3 and about pH 8, or between about pH 3.5 and about pH 7.5.

The increase of the viscosity above 150 cP and formation of the plug is done in a time less than 10 minutes or even less than 5 minutes, to allow quick formation of the plug.

The composition can be made in an aqueous solution. The aqueous solution may be fresh water or an aqueous solution comprising mono, di or trivalent metal salts, ammonium or mixtures of these. The salt can be present naturally if brine is used, or can be added to the aqueous solution. For example, it is possible to add to water; any salt, such as an alkali metal or alkali earth metal salt ($NaCO_3$, NaCl, KCl, etc.). The salt is generally present in weight percent concentration between about 0.1% to about 5%, from about 1% to about 3% by weight. One useful concentration is about 2% by weight. For some applications, in particular where freezing might be expected, the aqueous solution may further comprises an alcohol such as methanol, ethanol, propanol or a polyalcohol such a glycol or polyglycols or mixture thereof.

The polymer able to be hydrated may be any crosslinking polymers. The polymer can be a metal-crosslinking polymer. Suitable polymers for making the metal-crosslinked polymer include, for example, polysaccharides such as substituted galactomannans, such as guar gums, high-molecular weight polysaccharides composed of mannose and galactose sugars, or guar derivatives such as cationic guar derivatives such as Guar hydroxypropyltrimonium chloride and alike hydroxypropyl guar (HPG), carboxymethylhydroxypropyl guar (CMHPG) and carboxymethyl guar (CMG), hydrophobically modified guars, guar-containing compounds, and synthetic polymers. Crosslinking agents based on boron, titanium, zirconium or aluminum complexes are typically used to increase the effective molecular weight of the polymer and make them better suited for use in high-temperature wells.

Other suitable classes of polymers include polyvinyl polymers, polymethacrylamides, cellulose ethers, lignosulfonates, and ammonium, chitosan alkali metal, and alkaline earth salts thereof. More specific examples of other typical water soluble polymers are acrylic acid-acrylamide copolymers, acrylic acid-methacrylamide copolymers, polyacrylamides, partially hydrolyzed polyacrylamides, partially hydrolyzed polymethacrylamides, polyvinyl alcohol, polyalkyleneoxides, other galactomannans, heteropolysaccharides obtained by the fermentation of starch-derived sugar and ammonium and alkali metal salts thereof.

Cellulose derivatives are used to a smaller extent, such as hydroxyethylcellulose (HEC) or hydroxypropylcellulose (HPC), carboxymethylhydroxyethylcellulose (CMHEC) and carboxymethycellulose (CMC), with or without crosslinkers.

Xanthan, diutan, and scleroglucan, three biopolymers, have been shown to have excellent particulate-suspension ability even though they are more expensive than guar derivatives and therefore have been used less frequently, unless they can be used at lower concentrations.

In other embodiments, the polymer is made from a crosslinkable, hydratable polymer and a delayed crosslinking agent, wherein the crosslinking agent comprises a complex comprising a metal and a first ligand selected from the group consisting of amino acids, phosphono acids, and salts or derivatives thereof. Also the crosslinked polymer can be made from a polymer comprising pendant ionic moieties, a surfactant comprising oppositely charged moieties, a clay stabilizer, a borate source, and a metal crosslinker. Said embodiments are described in U.S. Patent Publications US2008-0280790 and US2008-0280788 respectively, each of which are incorporated herein by reference.

The pH trigger may be organic or inorganic acid. The pH trigger may be liquid, solid or encapsulated acid. The pH trigger can be encapsulated in a microsphere, or in an emulsion or suspension in some liquid carrier.

In one embodiment, the pH trigger is an encapsulated acid with a protective coating. The protective coating is able to be deteriorated by change of temperature by substantially not by time. In other embodiment, the protective coating is able to be deteriorated by change of temperature and also by time.

In one embodiment, the polymer used is guar derivative biopolymer. These biopolymers require specific pH range to hydrate. Outside of that pH range hydration is either very slow or does not proceed at all. In case of guar gum derivatives pH dependence of hydration rate can be attributed to the specific manufacturing process. One of the stages of manufacturing process includes mild crosslinking of guar splits with borates. The crosslinking reaction occurs at basic pH (usually higher than 9) and the resulting polymer has basic properties. Borate crosslinks that remain stable at pH above 8.5-9, hold guar molecules together preventing water molecules from penetrating inside the polymer grains and thus slowing down the hydration. Once the crosslinks have been chemically removed by decreasing the pH the polymer molecules unwrap and hydration occurs instantaneously resulting in swelling of polymer grains and dramatic viscosity increase.

An example of pH dependence of hydration is given on FIG. 1, where 1.25% (by weight) CMHPG suspension in water does not hydrate and therefore develop any viscosity at pH, 10.5 11.0 and 11.6. Once pH is reduced to 7.7 with a few drops of HCl the hydration occurs instantaneously resulting in sharp viscosity increase.

The composition may further comprise a degradable material. The degradable material may be degradable fibers or particles made of degradable polymers. The differing molecular structures of the degradable materials that are suitable give a wide range of possibilities regarding regulating the degradation rate of the degradable material. In choosing the appropriate degradable material, one should consider the degradation products that will result. For instance, some may form an acid upon degradation, and the presence of the acid may be undesirable; others may form degradation products that would be insoluble, and these may be undesirable. Moreover, these degradation products should not adversely affect other operations or components.

The degradability of a polymer depends at least in part on its backbone structure. One of the more common structural characteristics is the presence of hydrolyzable and/or oxidizable linkages in the backbone. The rates of degradation of, for example, polyesters, are dependent on the type of repeat unit, composition, sequence, length, molecular geometry, molecular weight, morphology (e.g., crystallinity, size of spherulites, and orientation), hydrophilicity, surface area, and additives. Also, the environment to which the polymer is subjected may affect how the polymer degrades, e.g., temperature, presence of moisture, oxygen, microorganisms, enzymes, pH, and the like. One of ordinary skill in the art, with the benefit of this disclosure, will be able to determine what the optimum polymer would be for a given application considering the characteristics of the polymer utilized and the environment to which it will be subjected.

Suitable examples of polymers that may be used include, but are not limited to, homopolymers, random aliphatic polyester copolymers, block aliphatic polyester copolymers, star aliphatic polyester copolymers, or hyperbranched aliphatic polyester copolymers. Such suitable polymers may be prepared by polycondensation reactions, ring-opening polymerizations, free radical polymerizations, anionic polymerizations, carbocationic polymerizations, coordinative ring-opening polymerization for, such as, lactones, and any other suitable process. Specific examples of suitable polymers include polysaccharides such as dextran or cellulose; chitins; chitosans; proteins; aliphatic polyesters; poly(lactides); poly(glycolides); poly($\epsilon$-caprolactones); poly(hydroxy ester ethers); poly(hydroxybutyrates); polyanhydrides; polycarbonates; poly(orthoesters); poly(acetals); poly(acrylates); poly(alkylacrylates); poly(amino acids); poly(ethylene oxide); poly ether esters; polyester amides; polyamides; polyphosphazenes; and copolymers or blends thereof. Other degradable polymers that are subject to hydrolytic degradation also may be suitable. One guideline for choosing which composite particles to use in a particular application is what degradation products will result. Another guideline is the conditions surrounding a particular application.

Of these suitable polymers, aliphatic polyesters are preferred. Of the suitable aliphatic polyesters, polyesters of $\alpha$ or $\beta$ hydroxy acids are preferred. Poly(lactide) is most preferred. Poly(lactide) is synthesized either from lactic acid by a condensation reaction or more commonly by ring-opening polymerization of cyclic lactide monomer. The lactide monomer exists generally in three different forms: two stereoisomers L- and D-lactide; and D,L-lactide (meso-lactide). The chirality of the lactide units provides a means to adjust, inter alia, degradation rates, as well as the physical and mechanical properties after the lactide is polymerized. Poly(L-lactide), for instance, is a semicrystalline polymer with a relatively slow hydrolysis rate. This could be desirable in applications where slow degradation of the degradable material is desired. Poly(D,L-lactide) is an amorphous polymer with a much faster hydrolysis rate. The stereoisomers of lactic acid may be used individually or combined for use in the compositions and methods of the present embodiments. Additionally, they may be copolymerized with, for example, glycolide or other monomers like $\epsilon$-caprolactone, 1,5-dioxepan-2-one, trimethylene carbonate, or other suitable monomers to obtain polymers with different properties or degradation times. Additionally, the lactic acid stereoisomers can be modified by blending high and low molecular weight polylactide or by blending polylactide with other aliphatic polyesters. For example, the degradation rate of polylactic acid may be affected by blending, for example, high and low molecular weight polylactides; mixtures of polylactide and lactide monomer; or by blending polylactide with other aliphatic polyesters.

The physical properties of degradable polymers may depend on several factors such as the composition of the repeat units, flexibility of the chain, presence of polar groups, molecular mass, degree of branching, crystallinity, orientation, etc. For example, short chain branches reduce the degree of crystallinity of polymers while long chain branches lower the melt viscosity and impart, inter alia, extensional viscosity with tension-stiffening behavior. The properties of the material utilized can be further tailored by blending, and copolymerizing it with another polymer, or by a change in the macromolecular architecture (e.g., hyper-branched polymers, star-shaped, or dendrimers, etc.). The properties of any such suitable degradable polymers (such as hydrophilicity, rate of biodegration, etc.) can be tailored by introducing functional groups along the polymer chains. One of ordinary skill in the art, with the benefit of this disclosure, will be able to determine the appropriate functional groups to introduce to the polymer chains to achieve the desired effect.

In some embodiments, the degradable materials are in the form of beads, powder, spheres, ribbons, platelets, fibers, flakes, or any other shape with an aspect ratio equal to or greater than one. In some embodiments, the degradable materials include particles having an aspect ratio greater than 10, greater than 100, greater than 200, greater than 250 or the like, such as platelets or fibers or the like. The blended materials can take any form of composites, for example biodegradable material coatings or scaffolds with other materials dispersed therein. Further, the degradable particles can be nano-, micro-, or mesoporous structures that are fractal or non-fractal.

According to a further embodiment, the composition may further comprise additives as breakers, anti-oxidants, corrosion inhibitors, delay agents, biocides, buffers, fluid loss additives, pH control agents, solid acids, solid acid precursors, organic scale inhibitors, inorganic scale inhibitors, demulsifying agents, paraffin inhibitors, corrosion inhibitors, gas hydrate inhibitors, asphaltene treating chemicals, foaming agents, fluid loss agents, water blocking agents, EOR enhancing agents, or the like. The additive may also be a biological agent.

The composition is compatible with other fluids or material as for example hydrocarbons such as mineral oil, proppants or additives normally found in well stimulation. Current embodiments can be used in various applications including temporary plugs formation, kill plugs, or multiple fracturing steps for to treating subterranean formations having a plurality of zones of differing permeabilities.

The method comprises injecting into a wellbore, the composition and allowing viscosity of the composition to increase and form a plug. Application could be used for fracture stimulation treatments in new or refraced horizontal or vertical wells to achieve near-wellbore diversion by opening entirely new zones to the treatment or restimulation that effectively extends the former stimulation within an older pre-existing fractured zone.

To facilitate a better understanding of some embodiments, the following examples of embodiments are given. In no way should the following examples be read to limit, or define, the scope of the embodiments described herewith.

EXAMPLES

Series of experiments were conducted to demonstrate properties of compositions and methods as disclosed above.

Example 1

5% (by weight) CMHPG suspension in water was prepared by blending 10 g of CMHPG powder with 200 ml of DI water. pH was further adjusted to 10 with 2 drops of 10% NaOH solution. The resulting blend does not develop any viscosity for 24 hours at room temperature.

A few drops of concentrated HCl were added to the freshly prepared 5% CMHPG suspension so pH drops to 6.6. Upon addition of the acid the system develops high viscosity instantaneously. In a few seconds it completely solidifies.

Example 2

5% (by weight) Cationic Guar (Ecopol 14) suspension in water was prepared by blending 10 g of Ecopol 14 powder with 200 ml of DI water. pH was further adjusted to 10 with 2 drops of 10% NaOH solution. The resulting blend does not develop any viscosity for 24 hours at room temperature.

A gram of fumaric acid was added to the freshly prepared 5% Ecopol 14 suspension so pH drops to 3.2. Upon addition of the acid the system develops high viscosity instantaneously. In a few seconds it completely solidifies.

Example 3

5% (by weight) Cationic Guar (Ecopol 14) suspension in water was prepared by blending 10 g of Ecopol 14 powder with 200 ml of DI water. 0.2 g of encapsulated ammonium persulfate was added to the mixture. pH was further adjusted to 10 with few drops of 10% NaOH solution. The resulting blend does not develop any viscosity for 24 hours at room temperature.

A gram of fumaric acid was added to the freshly prepared 5% Ecopol 14 suspension so pH drops to 3.0. Upon addition of the acid the system develops high viscosity instantaneously. In a few seconds it completely solidifies.

The system was then placed in oven at 150 F to assist the release of ammonium persulfate from encapsulation. After 24 hours polymer viscous pill was completely broken resulting in fluid with water like consistency.

Example 4

1.5% (by weight) Cationic Guar (Ecopol 14) suspension in water was prepared by blending 3 g of Ecopol 14 powder with 200 ml of DI water. pH was further adjusted to 10 with few drops of 10% NaOH solution. The resulting blend was tested on Grace 5600 rheometer at 100 c$^{-1}$ and temperatures 70-180 F. After 3 hours no viscosity development was observed.

Another two samples of 1.5% (by weight) Cationic Guar (Ecopol 14) suspension were prepared in the same way.

Figure 2:
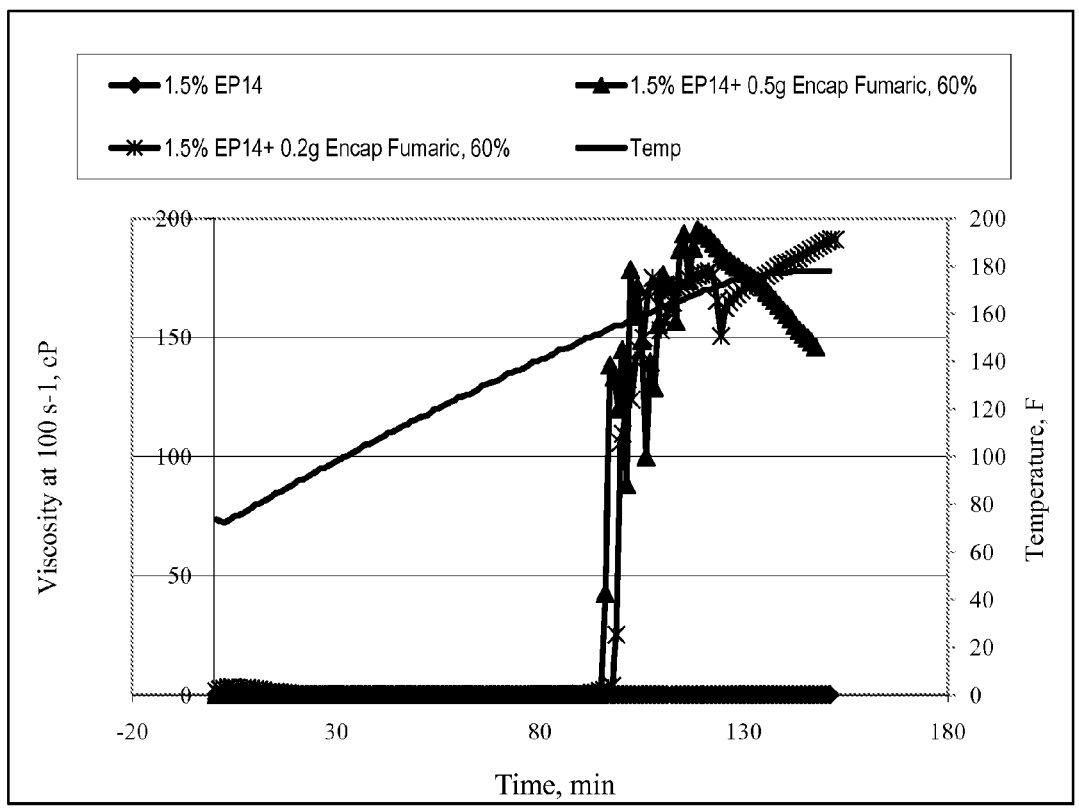
FIG. 2 is a graph showing polymer hydration according to one embodiment promoted by temperature triggered release of acid.

Prior to testing them on Grace 5600, 0.2 and 0.5 grams of encapsulated fumaric acid (60% active content) were added into the rheometer cups respectively. The same temperature program was used for testing. In both cases once the temperature triggered the release of fumaric acid from encapsulation a rapid hydration with instantaneous increase in viscosity was observed. FIG. 2 shows the results of those tests.

Example 5

5% (by weight) Cationic Guar (Ecopol 17) suspension in water was prepared by blending 10 g of Ecopol 17 powder with 200 ml of DI water. pH was further adjusted to 10 with few drops of 10% NaOH solution. The resulting blend was tested on Grace 5600 rheometer at 100 c$^{-1}$ and temperatures 70-180 F. After 3 hours no viscosity development was observed.

Another two samples of 5% (by weight) Cationic Guar (Ecopol 17) suspension were prepared in the same way.

Figure 3:
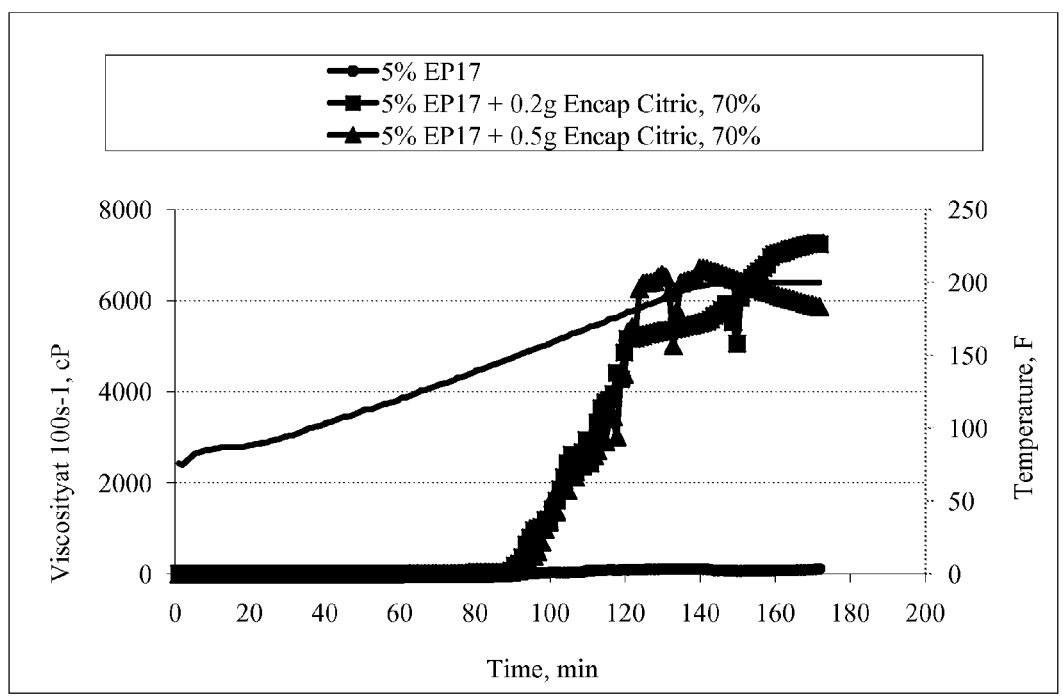
FIG. 3 is a graph showing polymer hydration according to a second embodiment promoted by temperature triggered release of acid.

Prior to testing them on Grace 5600, 0.2 and 0.5 grams of encapsulated citric acid (70% active content) were added into the rheometer cups respectively. The same temperature program was used for testing. In both cases once the temperature triggered the release of citric acid from encapsulation a rapid hydration with instantaneous increase in viscosity was observed. FIG. 3 shows the results of those tests.

The particular embodiments disclosed above are illustrative only, as the invention may be modified and practiced in different but equivalent manners apparent to those skilled in the art having the benefit of the teachings herein. Furthermore, no limitations are intended to the details herein shown, other than as described in the claims below. It is therefore evident that the particular embodiments disclosed above may be altered or modified and all such variations are considered within the scope of the embodiments described herewith. Accordingly, the protection sought herein is as set forth in the claims below.

What is claimed is:

1. A method of zonal isolation or diversion in a wellbore, the method comprising:
    a. providing a composition comprising
        a pH trigger selected from the group consisting of organic acid, inorganic acid, encapsulated acid, latent acid, acid emulsion, acid suspension and mixture thereof, and
        a polymer able to be hydrated in a defined pH range, wherein the composition has a pH outside of the defined pH range;
    b. injecting the composition into a wellbore; and
    c. triggering the pH trigger to lower the pH of the composition to a pH within the defined pH range, wherein the polymer is hydrated at the pH within the defined pH range, which allows a viscosity of the composition to increase and form a plug.

2. The method of claim 1, wherein the polymer is selected from the group consisting of diutan, xanthan, guar, guar derivatives and mixture thereof.

3. The method of claim 2, wherein the polymer is selected from the group consisting of CMHPG, CMG, HPG, cationic guar derivatives such as guar hydroxypropyltrimonium chloride and alike and mixture thereof.

4. The method of claim 1, wherein the polymer is in concentration between about 1 and about 15% by weight.

5. The method of claim 1, wherein the defined pH range is between about 2 and about 8.

6. The method of claim 5, wherein the defined pH range is between about 3.5 and about 7.5.

7. The method of claim 1, wherein the step of forming a plug is done in a time less than 10 minutes.

8. The method of claim 7, wherein the step of forming a plug is done in a time less than 5 minutes.

9. The method of claim 1, wherein encapsulated acid comprises a protective coating and an acid, the protective coating being degradable with temperature.

10. The method of claim 1, wherein encapsulated acid comprises a protective coating and an acid, the protective coating being degradable with time.

11. The method of claim 1, wherein the composition further comprises a degradable material.

12. The method of claim 11, wherein the degradable material is a PLA fiber.

13. The method of claim 1, wherein the composition further comprises a crosslinking agent.

14. The method of claim 1, wherein the composition further comprises a breaker.

15. A method of zonal isolation or diversion in a wellbore, the method comprising:

a. providing a composition comprising a polymer able to be hydrated in a defined pH range, wherein the composition has a pH outside of the defined pH range;
b. injecting the composition into a wellbore;
c. providing a pH trigger selected from the group consisting of organic acid, inorganic acid, encapsulated acid, latent acid, acid emulsion, acid suspension and mixture thereof; and
d. triggering the pH trigger to lower the pH of the composition to a pH within the defined pH range, wherein the polymer is hydrated at the pH within the defined pH range, which allows a viscosity of the composition to increase and form a plug.

16. The method of claim 15, wherein the pH trigger is injected into the wellbore with a tube.

17. The method of claim 16, wherein the tube is selected from the group consisting of casing, microcoil, coil tubing, producing tubing, tube from a downhole tool and combination thereof.

18. The method of claim 15, wherein the step of forming a plug is done in a time less than 10 minutes.

19. The method of claim 18, wherein the step of forming a plug is done in a time less than 5 minutes.

20. A method of zonal isolation or diversion in a wellbore the method comprising:

a. providing a composition comprising a polymer able to be hydrated in a defined pH range, wherein the composition has a pH outside of the defined pH range;
b. injecting the composition into a wellbore;
c. providing a pH trigger selected from the group consisting of organic acid, inorganic acid, encapsulated acid, latent acid, acid emulsion, acid suspension and mixture thereof;
d. triggering the pH trigger to lower the pH of the composition to a pH within the defined pH range, wherein lowering the pH removes crosslinks from the polymer; and
e. after the crosslinks have been removed, hydrating the polymer at the pH within the defined pH range to allow a viscosity of the composition to increase above 150 cP and form a plug.

21. The method of claim 20, wherein the pH trigger is injected into the wellbore with a tube.

22. The method of claim 21, wherein the tube is selected from the group consisting of casing, microcoil, coil tubing, producing tubing, tube from a downhole tool and combination thereof.

23. The method of claim 20, wherein the pH trigger is injected into the composition prior to injecting the composition in the wellbore.

* * * * *